United States Patent
Bodenschatz et al.

(10) Patent No.: US 6,267,743 B1
(45) Date of Patent: Jul. 31, 2001

(54) ANATOMICALLY SHAPED MEDICAL BANDAGES

(75) Inventors: Stefan Bodenschatz, Buxtehude; Thorsten Herzberg, Hamburg, both of (DE); Frank Doheny, Thurles (IL)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 08/989,583

(22) Filed: Dec. 12, 1997

(30) Foreign Application Priority Data

Dec. 13, 1996 (DE) .............................. 196 51 912

(51) Int. Cl.[7] .................................................. A61F 13/00
(52) U.S. Cl. ................ 602/62; 602/60; 602/61; 602/63; 602/64
(58) Field of Search ................ 602/60, 65, 5, 602/7, 20, 21, 26, 27, 6, 8, 10, 22, 61, 62

(56) References Cited

U.S. PATENT DOCUMENTS

| | | | |
|---|---|---|---|
| 4,006,542 | 2/1977 | Larson | 36/43 |
| 4,019,505 | 4/1977 | Wartman | 128/90 |
| 4,193,395 | 3/1980 | Guber | 128/90 |
| 4,273,115 | * 6/1981 | Holland et al. | 602/8 |
| 4,522,203 | * 6/1985 | Mays | 428/287 |
| 4,572,167 | 2/1986 | Brunswick | 128/78 |
| 4,622,260 | * 11/1986 | Tesch | 428/173 |
| 4,684,570 | 8/1987 | Malaney | 428/296 |
| 4,846,822 | 7/1989 | Foxman | 604/370 |
| 5,072,725 | 12/1991 | Miller | 128/78 |
| 5,268,222 | 12/1993 | Honeycutt | 428/224 |
| 5,356,371 | 10/1994 | Hubbard | 602/22 |
| 5,573,501 | * 11/1996 | Ruscito et al. | 602/7 |

FOREIGN PATENT DOCUMENTS

| | | |
|---|---|---|
| 324540 | 9/1975 | (AT) . |
| 706337 | 5/1941 | (DE) . |
| 1722817 | 2/1956 | (DE) . |
| 1013393 | 8/1957 | (DE) . |
| 1491214 | 5/1969 | (DE) . |
| 1812146 | 6/1970 | (DE) . |
| 2758216 | 6/1978 | (DE) . |
| 8119906.6 | 7/1981 | (DE) . |
| 3240933 | 5/1983 | (DE) . |
| 3729262 | 3/1989 | (DE) . |
| 8902447.8 | 6/1989 | (DE) . |
| 4091302 | 11/1991 | (DE) . |
| 4031943 | 4/1992 | (DE) . |
| 4203130 | 8/1992 | (DE) . |
| 19506128 | 8/1996 | (DE) . |
| 2615396 | 11/1988 | (FR) . |
| 2298140 | 8/1996 | (GB) . |
| WO 95/26698 | 10/1995 | (WO) . |
| WO 95/26699 | 10/1995 | (WO) . |
| WO 95/33426 | 12/1995 | (WO) . |

\* cited by examiner

Primary Examiner—Kim M. Lewis
(74) Attorney, Agent, or Firm—Norris McLaughlin & Marcus

(57) ABSTRACT

Medical bandages which are adapted to the shape of the body part on which they are applied, and which are characterized in that the soft and adaptable material has been thermally deformed.

11 Claims, 3 Drawing Sheets

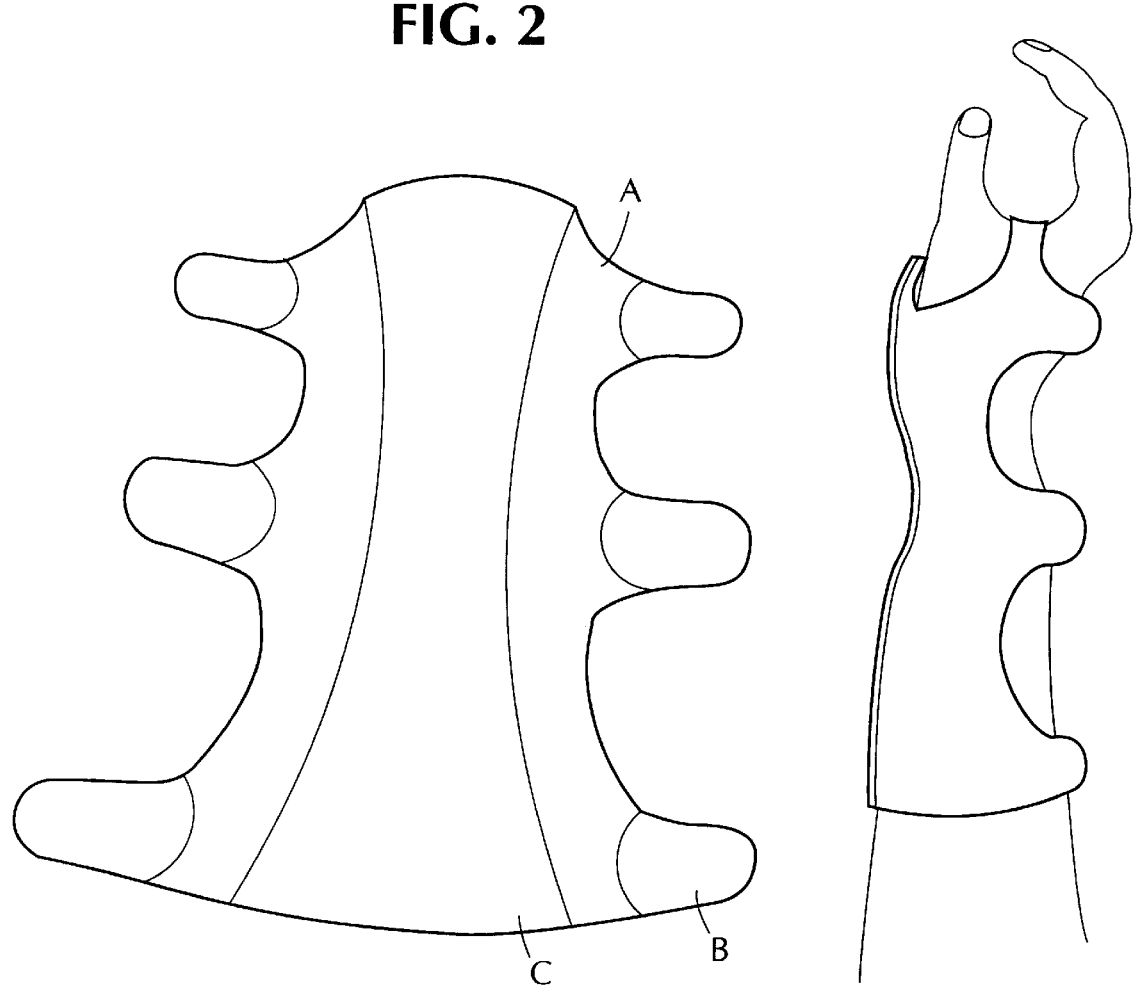

ANATOMICALLY SHAPED MEDICAL BANDAGES

The invention relates to medical bandages which are adapted to the shape of the body part on which they are to be applied.

BACKGROUND OF THE INVENTION

Depending on their construction and their field of indication, medical bandages of this kind essentially exert a fixing, guiding, supporting or compressing action on the corresponding body part, such as, for example, the limbs. They are also used in the treatment of burn wounds.

The bandages are produced by cutting out suitable blanks from planar material, such as, for example, more or less elastic woven fabrics or knits, foam materials, e.g. neoprene, and the like. The anatomically adapted shape is in this case achieved by the shape of the blanks and their subsequent joining together, if appropriate also with additional darting and gusseting, as is also normal procedure in the manufacture of clothing.

The joining together is normally done by sewing or gluing. The great disadvantage of this is that an exact anatomical fit of the bandages can be achieved only with difficulty, and a large number of connecting points, such as seams, are often created. These connecting points partially alter the properties of the material used, e.g. its elastic properties and adaptability, and this poses in particular the risk of pressure points or chafing points on the skin.

This occurs most often in the case of compression stockings and bandages for burns. The bandages for burns have a large number of seams, for example in the region of the female breast or in the facial region, and these can lead to painful pressure points.

Another possible way of producing medical bandages is the shaped knitting with flat knitting machines or circular knitting machines. However, this method is limited in terms of the possibility of shaping and the choice of material, especially since in most cases only two-dimensional shaping is possible and the third dimension has to be achieved again by means of connecting points such as seams. Such a method is also time-consuming.

Orthopaedic ortheses are also known in which foam rubber is deformed under pressure to different thicknesses and densities. In this way, functionally suitable designs can be made and the properties of the material can be locally altered (WO 95/32 690). However, these are relatively rigid standard products, and exact fitting to the anatomical shape is not achieved.

It is moreover known to shape thermoplastic plates in such a way as to give orthopaedic ortheses and prostheses of suitable form. The materials, e.g. HDPE or polypropylene and its copolymers, have a thermoplastic deformation range of approximately 170–250° C. and are substantially rigid after cooling, so that they cannot be used for soft and adaptable medical bandages.

SUMMARY OF THE INVENTION

The object of the invention was to avoid the said disadvantages and to produce medically effective bandages inexpensively and with a good fit.

This object was achieved by means of bandages according to claim 1.

BRIEF DESCRIPTION OF THE DRAWINGS

FIG. 2 shows a support bandage for the hand.

FIG. 3 shows the hand support bandage of FIG. 2 in use on a human hand.

DETAILED DESCRIPTION

Figure 1:
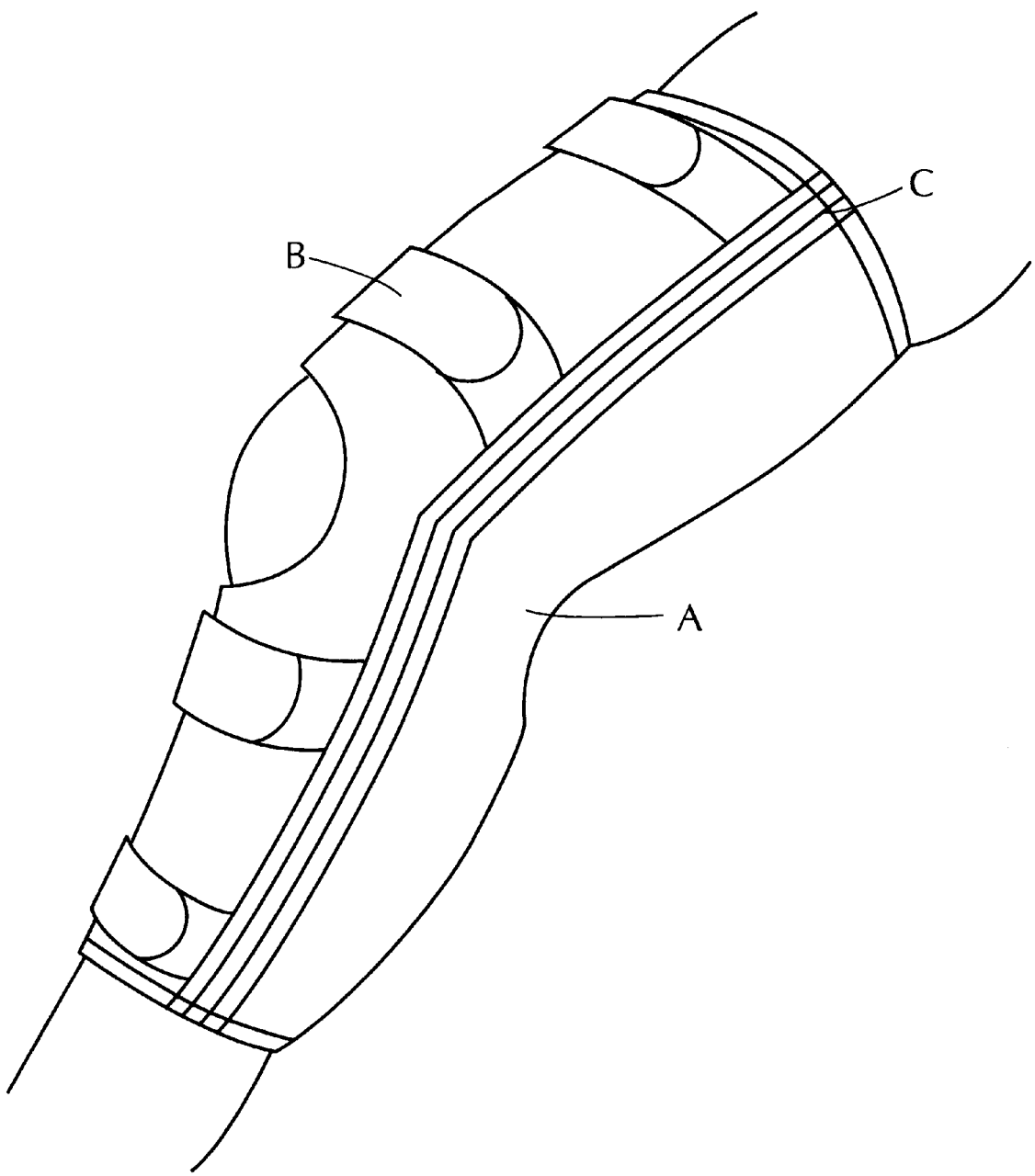
FIG. 1 shows a knee orthosis for immobilizing the knee joint.

Suitable materials for three-dimensional thermal deformation are all soft, adaptable materials from which such bandages are normally made, insofar as they have a thermoplastic character.

These are in particular nonwoven fabrics, woven fabrics, knits, film-type plastics with low rigidity, e.g. of LDPE, or foam materials. The materials can in this case consist wholly of thermoplastic base materials, or else they can contain only a proportion of such materials, which proportion must be sufficient, however, to ensure a good and stable deformability. Thus, for example, nonwoven fabrics, woven fabrics and knits can contain only a proportion of thermoplastically deformable fibres or filaments or other components such as binder. It is furthermore advantageous if these textile materials are designed elastically in one or more directions and for this reason contain at least a proportion of permanently elastic fibers or filaments, e.g. elastane or elastodiene.

The materials can be designed in a single layer, but can also consist of a two-layer or multi-layer laminate of thermoplastic character, for example of a thin foam material or a thin plastic plate which are lined on one side or on both sides with a textile.

The materials should be soft and adaptable, i.e. they are generally relatively thin. However, they can also have a certain thickness of 1 to several millimeters, so that, for example, sleeve-like and shell-like parts of a bandage can be produced from a thermo-plastically deformable nonwoven fabric of 5–20 mm thickness.

To be suitable for the intended purposes, the materials should moreover have a modulus of elasticity of less than 500 N/mm$^2$ (DIN 53 457) and a ball impression hardness of less than 35 N/mm$^2$ (DIN 53 457).

The thermal deformation can be carried out in various ways. One possibility is to heat the starting materials to the thermoplastic softening range and then to form them using positive molds which are shaped according to the anatomical conditions, for example by vacuum suction. It is also possible to use appropriately designed positive and negative molds. Another possibility is to process the cold or preheated material in heated molds. By means of the shaping it is additionally possible, e.g. in the case of nonwoven fabrics, to compress the material completely or partially.

For series production, the molds can correspond to normal anatomical sizes. For individual production, the molds are designed according to the individual anatomical conditions. This individual shaping can be based on a special scale model, a mould impression made of plaster, wax or the like, or a computer-assisted measurement method, e.g. scanning.

The shaped parts are then joined together to form medical bandages, if appropriate with other customary accessories, such as VELCRO closures, straps, splints, etc. The shaped parts can be incorporated in enclosing materials, preferably textile materials. However, it is often advantageous to design the bandages in such a way that the shaped starting materials can be used or processed without any enclosing material.

By using the invention it is possible to produce medical bandages which are configured according to the anatomical conditions. This is done by means of thermal deformation of the starting materials. It is possible to a large extent to dispense with troublesome connecting points. The products are additionally simple and inexpensive to produce since, to achieve the fit, they do not need to be joined or knitted together from a large number of parts which have been cut to size.

The invention is explained by the following examples:

EXAMPLE 1

A burns bandage for the face consists of a tubular elastic knit of nylon/elastane. The bandage is thermoplastically formed according to the anatomy of the head and in particular of the face. The molds chosen for shaping the bandage are designed such that the bandage has a defined undersize after shaping. This means that the elastic knit has to be stretched on application, so that it thereafter exerts pressure. This pressure can be distributed in a targeted manner across the facial region by means of the three-dimensional shaping and thus effectively prevent the formation of keloid bands which form ugly scars. Moreover, in the facial region there are no seams or other connecting points which could lead to pressure points.

EXAMPLE 2

FIG. 1 shows a knee orthosis for immobilizing the knee joint. The sleeve enclosing the leg is made of an approximately 10 mm thick nonwoven fabric A and is thermally formed to match the anatomy, so that it bears exactly on the leg. The sleeve is provided with conventional closures B. For improved stabilizing, conventional stiffening elements C can be provided.

EXAMPLE 3

FIG. 2 shows a support bandage for the hand, which bandage encloses the wrist as far as the forearm and is in the form of a sleeve made of an approximately 8 mm thick nonwoven fabric A and is thermally formed to match the anatomy. The sleeve is provided with conventional closures B. For improved stabilizing, conventional stiffening elements C can be provided. The bandage is shown on the left-hand side in the open state, and on the right-hand side in the state when applied to the hand. FIG. 3 shows the support bandage mounted on a hand.

EXAMPLE 4

Figure 4:
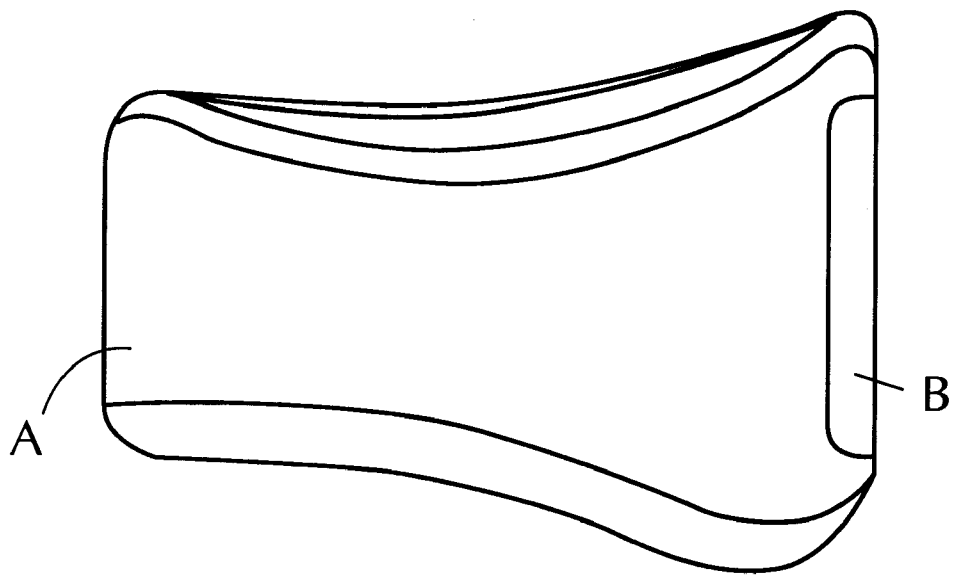
FIG. 4 shows a neck support.
Figure 5:
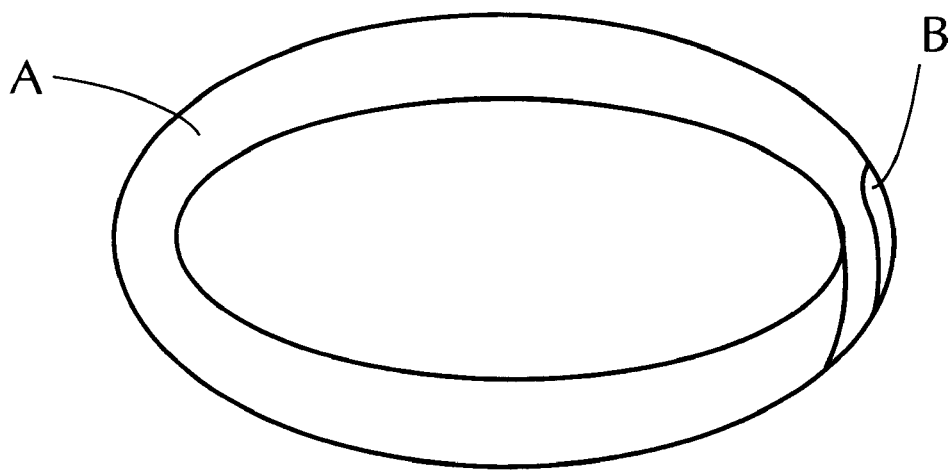
FIG. 5 shows the neck support of FIG. 4 in the closed state and in cross-section.

FIG. 4 shows a side view of a neck support in the closed position, made of an approximately 25 mm thick nonwoven fabric A which has been anatomically thermally formed 75.

What is claimed is:

1. A soft anatomically-shaped medical bandage, comprising a thermoplastically deformed material having a modulus of elasticity of less than 500 N/mm$^2$ and a ball impression hardness of less than 35 N/mm$^2$, wherein the bandage is formed into an anatomical shape by heating said bandage to the thermoplastic softening range of said material, forming the bandage into an anatomical shape, and cooling the material to retain said shape.

2. The medical bandage according to claim 1, wherein the bandage comprises thermoplastically deformed nonwoven fabrics, woven fabrics, knits, film or foam material.

3. The medical bandage according to claim 2, wherein the bandage in its entirety is thermoplastically deformed.

4. The medical bandage according to claim 2, wherein the bandage contains a proportion of thermoplastic fibers or components.

5. The medical bandage according to claim 1, wherein the bandage consists of a two-layer or multi-layer laminate, of which at least one layer is thermally deformed.

6. The medical bandage according to claim 1, wherein the thermally deformed parts of the bandage are surrounded by an enclosing material.

7. The medical bandage according to claim 1, wherein the bandage is heated to thermoplastic deformability and is then formed using a positive mold.

8. The medical bandage according to claim 1, wherein the material is heated to its thermoplastic deformability and is formed between a positive mold and negative mold.

9. The medical bandage according to claim 1, wherein the bandage is heated to its thermoplastic deformability in heated mold and is deformed.

10. The medical bandage according to claim 1, comprised only partially of thermoplastically deformed material.

11. The medical bandage according to claim 1, wherein the bandage has been thermoplastically formed according to individual body sizes.

\* \* \* \* \*